(12) United States Patent
McKim et al.

(10) Patent No.: US 6,555,726 B1
(45) Date of Patent: Apr. 29, 2003

(54) METHODS FOR ENHANCED EXTRACTIVE DISTILLATION EMPLOYING EXTRACTIVE DISTILLATION COMPOSITIONS COMPRISING SULFOLANE AND COMPATIBILITY AGENT

(75) Inventors: Artie S. McKim, Mandeville, LA (US); George Kvakovszky, Slidell, LA (US); Michael D. Donahue, The Woodlands, TX (US)

(73) Assignee: Gaylord Chemical Corporation, Slidell, LA (US)

( * ) Notice: Subject to any disclaimer, the term of this patent is extended or adjusted under 35 U.S.C. 154(b) by 0 days.

(21) Appl. No.: 09/448,651

(22) Filed: Nov. 10, 1999

(51) Int. Cl.$^7$ ............... C07C 7/10; C07C 7/00
(52) U.S. Cl. ............ 585/857; 585/833; 585/860; 585/864; 585/865; 585/866
(58) Field of Search ................ 585/833, 860, 585/864, 865, 866, 857

(56) References Cited

U.S. PATENT DOCUMENTS

| | | | |
|---|---|---|---|
| 2,033,942 A | 3/1936 | Kurtz | 208/321 |
| 2,831,039 A | 4/1958 | Nevitt | 324/450 |
| 3,146,190 A | 8/1964 | Papadopoulos | 208/313 |
| 3,466,346 A | 9/1969 | DeGraff | 203/56 |
| 3,714,033 A | 1/1973 | Somekh et al. | 208/321 |
| 3,723,256 A | 3/1973 | Thompson | 203/51 |
| 4,024,028 A | 5/1977 | Haskell | 203/51 |
| 4,053,369 A | 10/1977 | Cines | 263/52 |
| 4,081,355 A | 3/1978 | Preusser et al. | 208/313 |
| 4,292,142 A | 9/1981 | Berg | 203/51 |
| 4,401,517 A | 8/1983 | Lee | 203/53 |
| 4,676,872 A | 6/1987 | Berg et al. | 202/51 |
| 4,921,581 A | 5/1990 | Lee et al. | 203/56 |
| 4,948,470 A | 8/1990 | Lee | 203/51 |
| 5,032,232 A | 7/1991 | Lee et al. | 203/51 |
| 5,849,982 A | 12/1998 | Lee et al. | 585/833 |

OTHER PUBLICATIONS

Lee, F.M., "Extractive Distillation: Separating Close Boiling Components," Chemical Engineering, vol. 105, p. 112–118 (Nov. 1990).
H. Burrel, "Polymer Handbook," Second Edition, J. Brandrup and E. H. Immergut, Ed, Interscience, New York City, section IV, pp. 337–359 (1975).
"Jeffsol™ Carbonates, Comparative Solvents Data," published by Huntsman Corporation.
Sucksmith, "Extractive Distillation Saves Energy", Chemical Engineering, p. 91–95, Jun. 28, 1982.
Maas, "Continuous Distillation: Separation of Binary Mixtures", Handbook of Separation Techniques for Chemical Engineers, p. 1–135, McGraw Hill, 1979.
Perry s Chemical Engineers Handbook, Extractive Dist $6^{th}$ Ed., McGraw–Hill Book Company, pp. 13–53 to 13–57, 1984.
Lee, F.M, "Use of Organic Sulfones as the Extractive Distillation Solvent for Aromatics Recovery", Ind. Eng. Chem. Process Des. Dev., 25, 949–957 (1986).
Wu, et al., "Improve Operation and Design of BTX Units", Chemical Engineering, vol. 105, p. 139, Mar. 19998.
Barton, F.M., "Solubility Parameters" Chemical Reviews, 75(6), 731–753, (1975).
Barton, F.M.,Handbook of Solubility Parameters and Other Cohesion Parameters, CRC Press, p. 94–100, and 153–161, (1983).
Hansen, C.J., "The Three Dimensional Solubility Parameter–Key to Paint Component Affinities" (J. Paint Tech. 39, 104–117 (1967).

*Primary Examiner*—Walter D. Griffin
*Assistant Examiner*—Tam M. Nguyen
(74) *Attorney, Agent, or Firm*—Needle & Rosenberg, P.C.

(57) ABSTRACT

The invention relates to methods for enhanced extractive distillation of hydrocarbons that employ extrative distillation compositions comprising sulfolane or sulfolane derivatives in comination with compatibility agents.

28 Claims, 3 Drawing Sheets

METHODS FOR ENHANCED EXTRACTIVE DISTILLATION EMPLOYING EXTRACTIVE DISTILLATION COMPOSITIONS COMPRISING SULFOLANE AND COMPATIBILITY AGENT

FIELD OF THE INVENTION

This invention relates generally to compositions and processes for enhancing the separation of hydrocarbon compounds via extractive distillation.

BACKGROUND OF THE INVENTION

It is difficult to efficiently and economically separate mixtures of organic compounds having similar chemical characteristics, and nearly the same boiling point. Conventional fractional distillation can be expensive and inefficient in this situation, in that large and expensive columns are required, which have large numbers of plates, and utilize high reflux ratios with correspondingly high energy consumption rates.

Extractive distillation is a technique for separating certain close boiling mixtures. In extractive distillation, a high boiling solvent is typically introduced into a distillation zone above the entry point of the lower boiling feed mixture which is to be separated. The high-boiling solvent flows down the distillation zone, and interacts with the feed mixture, to effectively decrease the volatility of some mixture components, typically the more polar feed components, so that the less polar feed components can be distilled overhead, while the solvent and the more polar feed components exit the column with the bottoms fractions. An extractive distillation process has been described in the article entitled "Extractive Distillation Saves Energy" by Ian Sucksmith, Chemical Engineering, Jun. 28, 1982, pages 91–95. Other literature sources relating to extractive distillation techniques include the "Handbook of Separation Techniques for Chemical Engineers" by Philip A. Schweitzer, McGraw-Hill Book Company, 1979, pages 1–135; Perry's Chemical Engineers Handbook, 6th Edition, McGraw-Hill Book Company, 1984, pages 13–53.

The separation of various classes of hydrocarbons, such as aromatics, olefins, or cycloalkanes, from other close-boiling hydrocarbons, such as paraffins, by extractive distillation is known in the hydrocarbons industry. In particular, many refinery streams comprise "BTX streams" which comprise close-boiling mixtures of aliphatic hydrocarbons (such as isomers of heptane and octane) and aromatic hydrocarbons (such as benzene, toluene and xylenes). It is known in the industry to use mixtures of solvents such as various polyethylene glycol ethers and water as solvents for extractive distillation of hydrocarbon and/or BTX streams (i.e., "Udex" processes, and variations thereof). U.S. Pat. Nos. 3,714,033 and 4,921,581 disclose the use of polyalkylene glycol solvents toward this end.

Since the institution of "Udex" technology, efforts have been made to improve its production efficiency and economic performance in hydrocarbon separations by use of other types of solvents for extractive distillation. Morpholine derivatives and N-alkylpyrrolidones were disclosed as extractive distillation solvents, respectively, in U.S. Pat. Nos. 4,081,355 and 4,948,470. U.S. Pat. No. 4,676,872 discloses the use of adiponitrile in combination with other materials such as ethylene carbonate, nitrobenzene, and certain dialkyl phthalate esters, for the separation of xylene isomers. U.S. Pat. No. 4,292,142 discloses the use of phthalic anhydride in combination with other materials such as isophorone, for the separation of ethylbenzene from xylenes.

Other known processes have employed organic sulfones as solvents in extractive distillation processes. U.S. Pat. Nos. 2,033,942 and 2,831,039 described the use of dialkyl sulfones, including dimethylsulfone, in such separations. U.S. Pat. No. 4,401,517 relates to the use of $C_4$–$C_8$ sulfones as selective extractive distillation solvents, the preferred sulfone being di-n-propyl sulfone. U.S. Pat. No. 3,146,190 described the use of sulfolane (tetramethylene sulfone) as a selective extraction solvent for the purification of pyrolysis fuels and catalytically reformed gasolines. U.S. Pat. No. 3,466,346 describes further refinements of sulfolane based extractive distillation processes. U.S. Pat. No. 3,723,256 describes a method for utilizing sulfolane-type solvents in commercial units designed for glycol-based extractants. U.S. Pat. No. 4,053,369 describes methods for optimizing separation efficiencies in sulfolane based extractive distillation processes. Water-sulfolane mixtures are disclosed in U.S. Pat. No. 5,849,982.

Sulfolane is a known solvent for the extractive distillation of aromatic compounds from BTX streams in modem commercial hydrocarbon production. Sulfolane shows a reasonably good selectivity for separating aromatic materials from aliphatic compounds, but, Wu et.al estimate (Chemical Engineering, page 139, March 1998) that for a typical industrial BTX extraction unit, a 1% increase in aromatics recovery would result in savings of up to $100,000 per year. Such savings derive from both decreased need for capital investment, and decreased unit energy requirements (electricity, steam, etc) needed to perform the extractive distillation. Sulfolane also suffers from significant thermal degradation on an annual basis, and therefore requires regular makeup of its volume, which causes significant expense.

Relatively recent approaches to extraction medium modification involve the introduction of additives to sulfolane as a way of enhancing extraction performance. For example, U.S. Pat. No. 5,032,232 describes combinations of N-alkyl-2-thiopyrrolidones and sulfolane for this purpose. U.S. Pat. No. 4,024,028 describes the use of mixtures of dimethyl sulfone, methyl ethyl ketone and sulfolane for extractive distillation of certain hydrocarbon mixtures. Fu-Ming Lee (*Chemical Engineering*, Vol 105, pg112–118, November 1998) recently described the state of extractive distillation technology, and the use of sulfolane in combination with dialkyl sulfones, including dimethyl sulfone.

Thus, both technical and financial considerations provide a continuing need for developing novel and improved extractive distillation compositions which exhibit advantages (such as higher selectivity and/or capacity/loading) over known solvents for the extractive distillation of mixtures of close-boiling hydrocarbons.

SUMMARY OF THE INVENTION

The instant invention provides improved extractive distillation compositions and processes.

In one aspect, the invention relates to an extractive distillation composition for separating a mixture of hydrocarbon compounds comprising:
  a) sulfolane and/or a sulfolane derivative, and
  b) at least one compatibility agent, wherein the at least one compatibility agent:
    i) is selected from materials having a Polar Parameter and a Hydrogen Bonding Parameter such that the extractive distillation composition provides improved separation of the hydrocarbon compounds, as compared to the use of sulfolane and/or a sulfolane derivative without the compatibility agent;

ii) has a boiling point higher than the boiling point of the mixture of hydrocarbon compounds; and iii) does not comprise an N-substituted-2-thiopyrrolidone compound or residue.

In another aspect, the invention relates to a process for separating hydrocarbon compounds of similar boiling points by extractive distillation, comprising the steps of:

a) contacting a feed mixture with an extractive distillation composition within an extractive distillation zone, wherein the feed mixture comprises at least
  i) a first hydrocarbon compound, and
  ii) a second hydrocarbon compound; and b) distilling the feed mixture to at least partially separate the feed mixture into an overhead stream enriched in the first hydrocarbon compound, and a bottoms stream enriched in the second hydrocarbon compound; and wherein the extractive distillation composition comprises
  i) sulfolane and/or a sulfolane derivative, and
  ii) at least one compatibility agent, wherein the at least one compatibility agent:
    (1) is selected from materials having a Polar Parameter and a Hydrogen Bonding Parameter such that the extractive distillation composition provides improved separation of the hydrocarbon compounds, as compared to the use of sulfolane and/or a sulfolane derivative without the compatibility agent;
    (2) has a boiling point higher than the boiling point of the mixture of hydrocarbon compounds; and
    (3) does not comprise an N-substituted-2-thiopyrrolidone compound or residue.

In yet another aspect, the invention relates to a process for separating hydrocarbon compounds of similar boiling points by extractive distillation, comprising the steps of:

a) introducing a feed mixture into an extractive distillation zone having an upper portion and a lower portion, wherein the feed mixture comprises at least
  i) a first hydrocarbon compound comprising a $C_7$–$C_{10}$ aliphatic compound, and
  ii) a second hydrocarbon compound comprising benzene, toluene, ortho xylene, meta xylene, para xylene, or a mixture thereof;

b) introducing an extractive distillation composition into the upper portion of the extractive distillation zone;

c) distilling the feed mixture to at least partially separate the feed mixture into an overhead stream rich in the first hydrocarbon compound, and a bottoms stream rich in the second hydrocarbon compound;

wherein the extractive distillation composition comprises:
  i) about 100 parts by weight of sulfolane or a sulfolane derivative, and
  ii) from about 5 to about 35 parts by weight of a compatibility agent or a mixture of compatibility agents, wherein the compatibility agent comprises an unsubstituted or substituted derivative of acetophenone, propiophenone, benzonitrile, a dialkyl phthalate ester, a cinnamate ester, a $C_6$–$C_{12}$ alkyl ester of acetic, propionic, or butyric acid, a $C_7$–$C_{10}$ methyl alkyl ketone, isophorone, nitrobenzene, quinoline, or an isoquinoline.

In yet a different aspect, the invention relates to a process for separating a mixture of hydrocarbon compounds by extractive distillation that employs an extractive distillation composition, wherein the improvement comprises the use of an extractive distillation composition comprising:

a) sulfolane and/or a sulfolane derivative, and b) at least one compatibility agent, wherein the at least one compatibility agent:
  i) is selected from materials having a Polar Parameter and a Hydrogen Bonding Parameter such that the extractive distillation composition provides improved separation of the hydrocarbon compounds, as compared to the use of sulfolane and/or a sulfolane derivative without the compatibility agent;
  ii) has a boiling point higher than the boiling point of the mixture of hydrocarbon compounds; and
  iii) does not comprise an N-substituted-2-thiopyrrolidone compound or residue.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Figure 1:
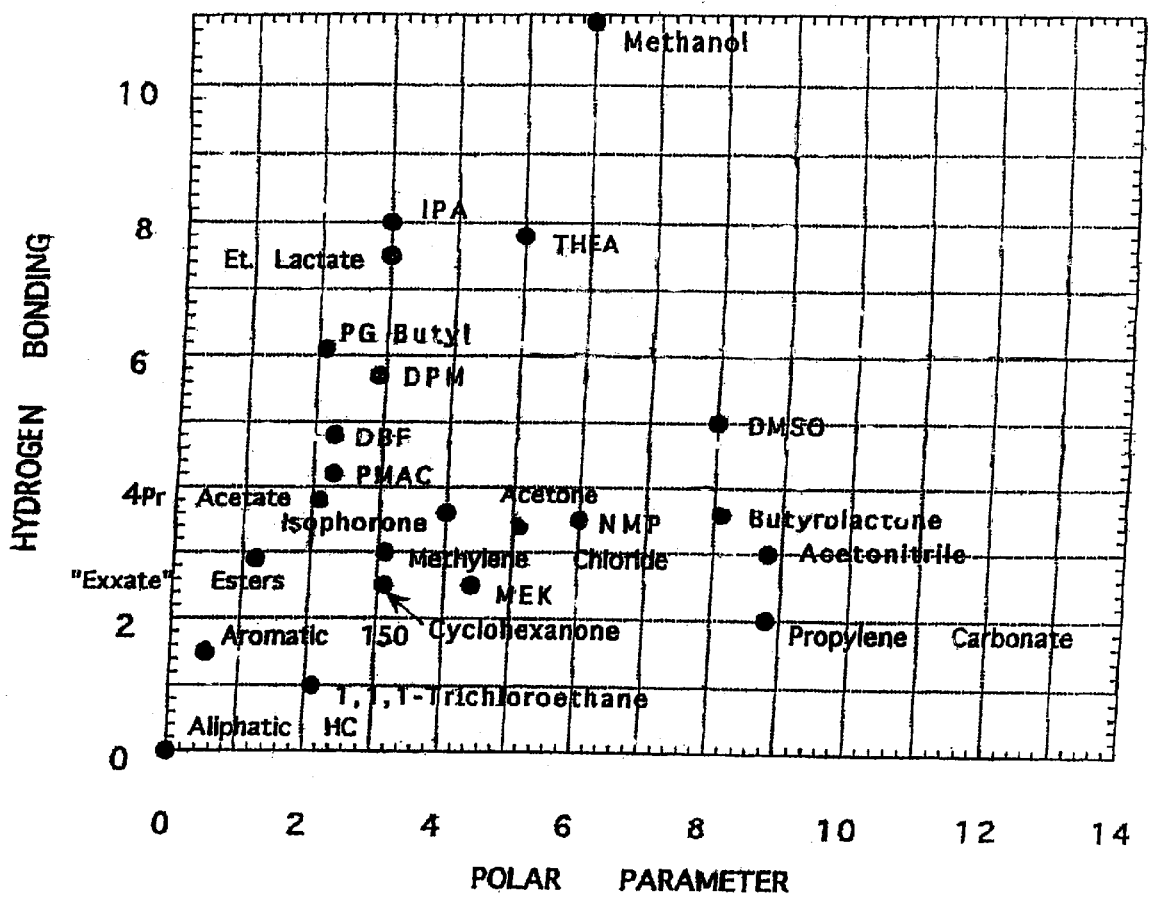
FIG. 1 shows a "map" of known Hansen's Solubility Hydrogen Bonding Parameters and Hansen's Solubility Polar Parameters for a number of readily available commercial solvents.

The present invention may be understood more readily by reference to the following detailed description of preferred embodiments of the invention and the Examples included therein.

Before the present compounds, compositions, articles, devices and/or methods are disclosed and described, it is to be understood that unless otherwise specifically stated by the claims, this invention is not limited to specific synthetic methods, specific types of distillation or fractionation equipment, methods of operating the distillation or fractionation equipment, or to particular ranges of temperature or pressure, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

References in the specification and concluding claims to parts by weight of a particular element or component in a composition or article denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain from 1 to 12 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms.

The term "alkylene" as used herein refers to a difunctional saturated branched or unbranched hydrocarbon chain containing from 1 to 24 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$—CH(CH$_3$)—CH$_2$—], hexylene [—(CH$_2$)$_6$—] and the like. "Lower alkylene" refers to an alkylene group of from 1 to 6, more preferably from 1 to 4, carbon atoms. The term "cycloalkylene" as used herein refers to a cyclic alkylene group, typically a 5- or 6-membered ring.

The term "aliphatic" as used herein describes branched or unbranched hydrocarbon chains or groups containing 1 to 24 carbon atoms which are saturated, i.e., they have no double bonds between the carbon atoms.

The term "aromatic" as used herein describes substituted or unsubstituted benzene-like compounds of six to twenty five carbon atoms having at least one 6-membered ring residue of carbon atoms, with alternating (conjugated) double bonds which have 4n+2π electrons, wherein n is a positive integer.

The term "heteroaromatic" as used herein describes describes substituted or unsubstituted compounds of two to twenty five carbon atoms, having at least one five or six membered ring residue having at least two carbon atoms, and at least one heteroatom in the ring residue comprising nitrogen, oxygen, or sulfur, with alternating (conjugated) double bonds and heteroatom lone pairs of electrons which have 4n+2π electrons, wherein n is a positive integer.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

As discussed above, one aspect of the invention relates to an extractive distillation composition for separating a mixture of hydrocarbon compounds. The extractive distillation composition includes a) sulfolane and/or a sulfolane derivative, and b) at least one compatibility agent.

The extractive distillation compositions of this invention are characterized by enhanced selectivity for the separation of key components of mixtures of hydrocarbon compounds, and by enhanced thermal stability, relative to extractive solvents currently available to refinery science.

Sulfolane, $C_4H_8SO_2$ (sometimes referred to as tetramethylene sulfone) or a sulfolane derivative, or mixtures of sulfolane and sulfolane derivatives provide at least a portion of the physical properties, solvency properties, and polarity properties, and hydrogen bonding properties which result in the desired selectivity for separating a mixture of hydrocarbon compounds. Sulfolane derivatives typically have the structure:

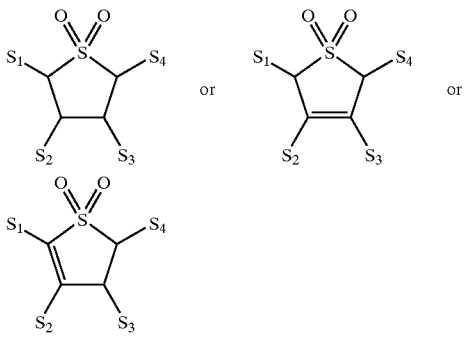

wherein the sulfolane derivatives have 0–4 substitutent groups ($S_1$, $S_2$, $S_3$, and $S_4$). The substituent groups are independently selected from a wide variety of organic and inorganic substitutent groups which are not substantially reactive under the conditions of extractive distillation. Suitable substituent groups for sulfolane a derivative include but are not limited to hydrogen, alkyl groups, alkoxy groups, aromatic groups, or, halides. Although sulfolane and sulfolane derivatives have a generally good thermal and chemical stability, they nevertheless undergo slow but significant thermal degradation over extended periods of time under the conditions typical of many extractive distillation processes.

The enhanced selectivity of the extractive distillation compositions of the invention are also related to the presence of at least one suitable compatibility agent. The compatibility agents of the invention are selected from materials that:

i) have a Polar Parameter and a Hydrogen Bonding Parameter such that the extractive distillation composition provides improved separation of the hydrocarbon compounds, as compared to the use of sulfolane and/or a sulfolane derivative without the compatibility agent;

ii) have a boiling point higher than the boiling point of the mixture of hydrocarbon compounds; and iii) does not comprise an N-substituted-2-thiopyrrolidone compound or residue.

While not wishing to be bound by any theory, the compatibility agents of the invention are believed to function as a material which influences or improves the interaction and/or solubility between the sulfolane or sulfolane derivatives (which are polar materials) and the mixture of hydrocarbon compounds (which are often non-polar materials). The compatibility agents of this invention are generally selected to have solvent solubility, dispersion, hydrogen bonding and/or polarity characteristics which are intermediate between the solvent solubility, dispersion, hydrogen bonding, and/or polarity characteristics of sulfolane and/or sulfolane derivatives, and the solvent solubility, dispersion, hydrogen bonding, and/or polarity characteristics of the mixture of hydrocarbon derivatives.

In general, compatibility agents so selected provide extractive distillation compositions which give improved separation of the hydrocarbon compounds, as compared to the use of a similar extractive distillation composition without the compatibility agent. The improved separation of the hydrocarbon compounds is generally reflected in greater selectivity of the separation, or higher purity, or higher capacity and/or loadings of the separated hydrocarbon compounds in various product streams which result from extractive distillation processes which employ the compatibility agents.

Additionally, the extractive distillation compositions of the invention, and the compatibility agents which are a component thereof, preferably have lower volatilities and/or higher boiling points than the boiling point of the mixture of hydrocarbon compounds. Preferably, the relatively higher boiling point of the compatibility agent prevents it from volatilizing to vapor, and the compatibility agent therefore tends to remain in a solution and/or liquid state, and flow downward toward the lower portion of a distillation zone, while interacting with, and separating components of the mixture of hydrocarbon compounds (which are present in both vapor and liquid phase) within the distillation zone. Because the feed mixtures of hydrocarbon compounds which are subjected to extractive distillation processes typically have normal boiling points below about 185° C., preferred compatibility agents for the compositions and processes of the invention have a normal boiling point exceeding 185° C. In more preferred embodiments of the invention, the compatibility agent has a normal boiling point from about 190° C. to about 400° C.

Numerous attempts have been made to define, quantify, or otherwise characterize the solvent solubility, dispersion, hydrogen bonding, and/or polarity characteristics of various solvents and chemical compounds and compositions, by various methods and systems. Allen F. M. Barton {Chemical Reviews, 75(6), 731–753 , (1975) ), and Handbook of Solubility Parameters and Other Cohesion Parameters, CRC Press, pg 94–110, and 153–161, (1983)} and H. Burrel {Polymer Handbook, $2^{nd}$ Ed., J. Brandrup and E. H. Immergut, Ed, Interscience, New York City, section IV, pages 337–359(1975)}, have described many of the various methods and systems of characterizing and quantifying solvent and/or solvency properties. The disclosure of these references regarding the methods and systems are hereby incorporated in their entirities by reference. Systems which characterize these physical characteristics by a single numerical "Solubility Parameter" (such as a Hildebrand Solubility Parameter), or a two component "Solubility Parameters" (polar and non-polar) are known. Such single parameter and double parameter systems are useful for selecting the compatibility agents of the instant invention.

Of even greater utility are "three component" or "three parameter" systems for characterizing the physical properties of solvents and chemical compounds. Three component or three parameter systems typically characterize chemical compounds by their "dispersion", "polar", and "hydrogen bonding" characteristics and/or "parameters". The "dispersion", "polar", and "hydrogen bonding" characteristics and/or "parameters" of a fairly wide variety of known materials have been determined by a variety of methods, based on a variety of types of experimental data and testing. Although it is impossible to measure such parameters for all the infinite number of possible chemical compounds, such parameters have been measured for hundreds or thousands of commonly available chemical compounds. Furthermore, a number of systems are now well established for experimentally determining" the "dispersion", "polar", and "hydrogen bonding" characteristics and/or "parameters" of most or all stable chemical compounds or compositions (single component or multi-component) which are of interest, with only routine and not excessive experimentation, which is within the average level of skill in the art.

In the methods provided by the instant invention, it has been found that superior compatibility agents can be selected by consideration of known or experimentally measured "polar" and/or "hydrogen bonding" characteristics and/or "parameters" of candidate compounds or compositions. The compatibility agents of the instant invention are preferably selected from materials having physical and/or solubility characteristics related to known or experimentally determinable "Polar Parameters" and "Hydrogen Bonding Parameters" which provide extractive distillation compositions which give improved separation of mixtures of hydrocarbon compounds in extractive distillation processes.

In many embodiments, the compatibility agents of the invention are a single chemical compound, selected on the basis of known or experimentally determinable Polar Parameters and Hydrogen Bonding Parameters. In other embodiments, the compatibility agent comprises a mixture of two or more materials, and the mixture of two or more materials has a Polar Parameter and a Hydrogen Bonding Parameter selected such that the extractive distillation composition provide improved separation of the hydrocarbon compounds. In yet other embodiments, the compatibility agent comprises a mixture of two or more materials, and each of the two or more materials has a Polar Parameter and a Hydrogen Bonding Parameter selected such that the extractive distillation composition provide improved separation of the hydrocarbon compounds.

Preferred compatibility agents have "Polar Parameters" and "Hydrogen Bonding Parameters" that are intermediate between the "Polar Parameters" and "Hydrogen Bonding Parameters" of the sulfolane and/or sulfolane derivatives contained in the compatibility agent, and the "Polar Parameters" and "Hydrogen Bonding Parameters" of the components of the mixture of hydrocarbon compounds which are to be separated by extractive distillation. The particular "Parameter System" utilized to quantify the physical characteristics which determine the "Polar Parameters" and "Hydrogen Bonding Parameters" of the potential compatibility agents is not critical to the practice of the invention.

One particularly well known and useful system for characterizing the "Polar Parameters" and "Hydrogen Bonding Parameters" of chemical compounds are "Hansen's Solubility Parameters." Hansen's Solubility Parameters take the general form $$\delta^2 \delta_d^2 + \delta_p^2 + \delta_h^2$$

wherein $\delta$ is the Hildebrand single parameter solubility parameter;

$\delta_d$ is the Hansen's Solubility Dispersive or Non-polar Parameter;

$\delta_p$ is the Hansen's Solubility Polar Parameter; and $\delta_h$ is the Hansen's Solubility Hydrogen Bonding Parameter;

Hansen's Solubility Parameters can be expressed in various units, including $(Mpa)^{1/2}$ (Mpa=Megapascals), or $(calories/cm^3)^{1/2}$. The units used to express the Hansen's Solubility Parameters are not critical, so long as internal consistency is maintained. Unless otherwise stated, the units of the Hansen's Solubility Parameters stated in this application are $(calories/cm^3)^{1/2}$. Protocols for experimentally determining the Hansen's Solubility Parameters of a given compound may be found in the references cited above, or the method described by Hansen (J. Paint Tech. 39, pg 505 (1967).

Hansen's Solubility Parameters have been determined for hundreds of common solvents and chemical compounds, as disclosed in the above-referenced articles by Barton and Burrel; by Barton in "Handbook of Solubilty Parameters and Other Cohesion Parameters", CRC Press pg 94–110, 153–161 (1983); by Technical Bulletin 1089–995, "Jeffsol" Carbonates, Comparative Solvents Data, published by Huntsman Corporation; and by Bulletin OP165-994-10M, Arcosolv Solvent Selector Chart, published by Lyondell Chemical; all of which are hereby incorporated by reference in their entirities. Examples of known Hansen's Solubility Parameters for 26 common solvents are shown in Table 1 below and FIG. 1.

As can be seen in Table 1, the Hansen's Dispersive Solubility Parameters ($\delta_d$) do not vary widely with the nature of the solvent/compound, but the Hansens Polar Solubility Parameters ($\delta_p$), and Hansen's Hydrogen Bonding Parameters ($\delta_h$), vary more widely with the nature of the solvent/compound, as can also be seen in the Hansen Commercial Solvent Map Shown in FIG. 1. The $\delta_p$ and $\delta_h$ of compounds such as alkanes are close to zero, but the $\delta_p$ and $\delta_h$ of polar compounds such as dimethyl sulfoxide are significantly higher.

In one preferred embodiment of the invention, suitable compatibility agents are selected from chemical compounds or compositions which has a Hansen's Solubility Polar Parameter from about 2.7 to about 6.4 $(calories/cm^3)^{1/2}$, and a Hansen's Solubility Hydrogen Bonding Parameter from about 1.0 to about 4.4 $(calories/cm^3)^{1/2}$. In a more preferred embodiment of the invention, suitable compatibility agents have a Hansen's Solubility Polar Parameter from about 3.2 to about 5.9 $(calories/cm^3)^{1/2}$, and a Hansen's Solubility Hydrogen Bonding Parameter from about 1.5 to about 3.9 $(calories/cm^3)^{1/2}$.

TABLE 1

HANSEN SOLUBILITY PARAMETERS-22 SOLVENT SET
(Units = $(calories/cm^3)^{1/2}$)

|  | SOLVENT | $\delta_d$ | $\delta_p$ | $\delta_h$ |
| --- | --- | --- | --- | --- |
| S-1 | Heptane | 7.5 | 0.0 | 0.0 |
| S-2 | Decaline | 8.8 | 0.0 | 0.0 |
| S-3 | Toluene | 8.8 | 0.7 | 1.0 |
| S-4 | Methylene Chloride | 8.9 | 3.1 | 3.0 |
| S-5 | Chlorobenzene | 9.3 | 2.1 | 1.0 |
| S-6 | Nitrobenzene | 9.8 | 4.2 | 2.0 |
| S-7 | Methanol | 7.4 | 6.0 | 10.9 |
| S-8 | Isopropanol | 7.7 | 3.0 | 8.0 |
| S-9 | n-Octanol | 8.3 | 1.6 | 5.8 |
| S-10 | Ethylene Glycol | 8.3 | 5.4 | 12.7 |
| S-11 | Dipropylene Glycol | 7.8 | 9.9 | 9.0 |
| S-12 | Tetrahydrofurfuryl Alcohol | 9.8 | 5.0 | 7.8 |
| S-13 | Dipropylene Glycol Dimethyl Ether | 7.4 | 3.0 | 6.3 |
| S-14 | Acetone | 7.6 | 5.1 | 3.4 |
| S-15 | Methyl Isobutyl Ketone | 7.5 | 3.0 | 2.0 |
| S-16 | Diacetone Alcohol | 7.7 | 4.0 | 5.3 |
| S-17 | Propylene Carbonate | 9.8 | 8.8 | 2.0 |
| S-18 | DBE ™ (Dibasic Esters from Dupont) | 8.3 | 2.3 | 4.8 |
| S-19 | Dimethylsulfoxide | 9.0 | 8.0 | 5.0 |
| S-20 | Acetontrile | 7.5 | 8.8 | 3.0 |
| S-21 | N-methyl-pyrrolidone | 8.8 | 6.0 | 3.5 |
| S-22 | Dimethylformamide | 8.5 | 6.7 | 5.5 |
|  | Gamma-butyrolactone | 9.3 | 8.1 | 3.6 |
|  | N,N-dimethylacetamide | 8.2 | 5.6 | 5.0 |
|  | Formamide | 8.4 | 12.8 | 9.3 |
|  | Triethylene glycol | 7.8 | 6.1 | 9.1 |

In some embodiments of the invention, the compatibility agent does not comprise an N-substituted-2-thiopyrrolidone residue or compound. In other embodiments of the invention, the compatibility agent does not comprise an N-substituted-pyrrolidone residue or compound.

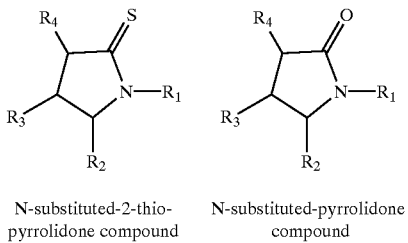

N-substituted-2-thio-pyrrolidone compound    N-substituted-pyrrolidone compound

The $R_1$—$R_4$ substituent groups of the N-substituted-2-thiopyrrolidone and/or N-substituted-pyrrolidone residues or compounds may independently comprise hydrogen, alkyl, alkylene, or aromatic groups, which may or may not be further substituted with groups such as hydroxy groups, alkoxy groups, amine groups, thiol groups, and the like.

In other embodiments of the invention, the compatibility agent does not comprise a monoalkyl ether of ethylene glycol, propylene glycol, or 1,4-butanediol, or a monoalkyl ether of polyether compounds derived from ethylene glycol, propylene glycol, 1,4-butanediol residues, or mixtures thereof.

In preferred embodiments of the invention, the compatibility agent comprises at least one substituted or unsubstituted derivative of:
a) acetophenone,
b) propiophenone,
c) benzonitrile,
d) a dialkyl phthalate ester,
e) a cinnamate ester,
f) a $C_6$–$C_{12}$ alkyl ester of acetic, propionic, or butyric acid,
g) a $C_7$–$C_{10}$ methyl-alkyl ketone,
h) isophrodne,
i) nitrobenzene,
j) quinoline, or isoquinoline, and
k) a dialkylester of succinic, glutaric, or adipic acids, or mixtures thereof.

Preferably, the above-described mixture of a dialkylester of succinic, glutaric, and adipic acids comprises the "Dibasic Esters"™ ("DBE") which is produced by DuPont Corporation, or a substantially equivalent mixture of dicarboxylic acid esters.

Preferred substituent groups for the substituted derivative compatibility agents described above include but are not limited to alkyl groups, alkoxy groups, aromatic groups, heteroaromatic groups, alcohol groups, aldehyde groups, ketone groups, carboxylic acid or ester groups, thiol or thio-ether groups, amine groups, amide groups, and the like. Preferably the compatibility agent comprises at least one aromatic residue.

In certain preferred embodiments of the invention, the compatibility agent comprises one or more of acetophenone, benzonitrile, di-n-butyl phthalate, diethyl phthalate, dimethyl phthalate, ethyl cinnamate, a 2-hexyl acetate, a methyl hexyl ketone, isophorone, nitrobenzene, or quinoline.

Preferably, the compatibility agent comprise from about 1 to about 50 parts by weight of the extractive distillation composition per 100 parts sulfolane and/or sulfolane derivative. More preferably, the compatibility agent comprise from about 5 to about 35 parts by weight of the extractive distillation composition. Most preferably, the compatibility agent comprise from about 15 to about 25 parts by weight of the extractive distillation composition.

In another preferred embodiment, the extractive distillation composition further comprises one or more dialkyl sulfones (in addition to the sulfolane or sulfolane derivative). More preferably, the dialkyl sulfones are selected from a group comprising dimethyl sulfone, and dialkyl sulfones of 3 to 9 carbon atoms.

Another preferred dialkyl sulfone is dimethyl sulfone ("$DMSO_2$"), i.e. $CH_3$—$SO_2$—$CH_3$. $DMSO_2$ is a high boiling, thermally stable material which is readily commercially available and relatively inexpensive. Moreover, $DMSO_2$ has solvency properties and extractive distillation behavior that is similar to sulfolane, but extends the recycle life of the extractive distillation composition, because of it's very high thermal stability. $DMSO_2$ effectively substitutes for sulfolane, which has a lower thermal stability than $DMSO_2$. This substitution allows the extractive distillation composition to be reused and recycled to a greater extent, minimizing make-up of the extractive distillation composition, and the associated expenditures.

Preferably, the extractive distillation composition comprises from about 0.1 parts to about 50 parts by weight of dimethylsulfone, per 100 parts of sulfolane and/or sulfolane derivative. More preferably, the extractive distillation composition comprises from about 10 parts to about 35 parts by weight of dimethylsulfone. Even more preferably, the extractive distillation composition comprises from about 15 parts to about 30 parts by weight of dimethylsulfone. A composition which is 36% dimethyl sulfone and 36% sulfolane by weight is an alternative especially preferred embodiment.

Small amounts of water may improve the selectivity of extractive distillation composition compositions for separation of the hydrocarbon compounds, lower the boiling point of the extractive distillation composition, and or improve miscibility of the components of the extractive distillation composition. Therefore, preferred embodiments of the extractive distillation composition of the invention may further comprise from about 0.1 parts to about 10 parts water per 100 parts of sulfolane and/or sulfolane derivative. More preferably, the extractive distillation further comprises from about 2 parts to about 5 parts water. The extractive distillation composition may advantageously comprise conventional surfactants, corrosion inhibitors, or antioxidants.

The above described extractive distillation compositions of the invention can be employed in a process for separating a mixture of hydrocarbon compounds by extractive distillation. The steps, apparatus, and operating procedures employed in the above-described embodiments of the extractive distillation processes of this invention are not limited to any particular set of steps, apparatus, or operating procedures, many variations of which are known to those of skill in the art, and are disclosed in the above-referenced patents.

Nevertheless, some preferred embodiments of the extractive distillation processes of the invention comprise the steps of:
a) contacting a feed mixture with an extractive distillation composition within an extractive distillation zone, wherein the feed mixture comprises at least
   i) a first hydrocarbon compound, and
   ii) a second hydrocarbon compound; and
b) distilling the feed mixture to at least partially separate the feed mixture into an overhead stream enriched in the first hydrocarbon compound, and a bottoms stream enriched in the second hydrocarbon compound; and wherein the extractive distillation composition comprises
i) sulfolane and/or a sulfolane derivative, and
ii) at least one compatibility agent, wherein the at least one compatibility agent:
   (1) is selected from materials having a Polar Parameter and a Hydrogen Bonding Parameter such that the extractive distillation composition provides improved separation of the hydrocarbon compounds, as compared to the use of sulfolane and/or a sulfolane derivative without the compatibility agent;
   (2) has a boiling point higher than the boiling point of the mixture of hydrocarbon compounds; and
   (3) does not comprise an N-substituted-2-thiopyrrolidone compound or residue.

In many embodiments of the processes of the invention, the feed mixture is introduced into an extractive distillation zone, which often has an upper portion and a lower portion. The extractive distillation zones suitable for the invention can comprise a wide variety of equipment, devices, suitable for distillation processes, such as tanks, vessels, pipes, tubing, heat exchangers, reboilers, wiped film or falling film evaporators, and the like. The extractive distillation zones are often provided with means for insuring intimate physical contact between the feed mixtures and the extractive distillation composition during the extractive distillation process, such as packing materials, condensers, and the like. The extractive distillation zones often comprise distillation columns, the design and operation of which are well known to those of skill in the art. The distillation columns may be packed with various materials which provide high surface areas, and/or insure a tortuous path for inducing mixing of gases and liquids. The distillation columns may also have trays, which collect liquid and have means for inducing the interaction of the liquid with vapors within the column.

Many embodiments of the extractive distillation processes of the invention comprise introducing the extractive distillation composition into the upper portion of the extractive distillation zone, so that it may flow downward as the distillation occurs, and intimately intermix with the feed mixture. The feed mixture is preferably introduced into a lower portion of the extractive distillation zone, so that the more volatile components vaporize and flow upward in the distillation zone. Preferably, the extractive distillation composition is not introduced at the uppermost portion of the extractive distillation zone, so as to insure that it does not contaminate the overhead stream, which is typically enriched in the more volatile and/or less polar components of the feed mixture, such as the first hydrocarbon compound. In a preferred embodiment, the extractive distillation process further comprises withdrawing the overhead stream from the upper portion of the extractive distillation zone.

The feed mixtures utilized in the extractive distillation processes can include complex mixtures of wide varieties of chemical compounds and/or hydrocarbons. Typically, the compounds comprise mixtures of hydrocarbon compounds and/or petroleum distillates, which may be unsubstituted, or substituted with a wide variety of alkyl groups, alkylene groups, aromatic groups, heteroatoms (including oxygen, nitrogen, silicon, sulfur, phosphorus or halogens), or heteroatomic groups or residues which contain heteroatoms. The hydrocarbon compounds may be branched or unbranched, saturated or unsaturated, cyclic or heterocyclic, aromatic, or substituted aromatic compounds.

In preferred embodiments, the feed mixture comprises a first hydrocarbon compound of relatively low polarity and/or hydrogen bonding capacity, and a second hydrocarbon compound having relatively higher polarity and/or hydrogen bonding capacity. For example, the feed mixture may comprise isomers with differing polarities, such as para-xylene and ortho-xylene. Preferably, the first hydrocarbon compound comprises at least one saturated hydrocarbon residue (exemplified by alkyl groups such as methyl and ethyl groups), and a second hydrocarbon compound comprising at least one carbon-carbon double bond (such as mono-olefins, polyolefins, and/or aromatics).

In many embodiments, the extractive distillation process at least partially separates the feed mixture into an overhead stream enriched in the first hydrocarbon compound, and a bottoms stream enriched in the second hydrocarbon compound. Often, the first hydrocarbon compound of the overhead stream is relatively non-polar as compared to the second hydrocarbon compound. While not wishing to be bound by theory, it is believed that the second hydrocarbon typically interacts relatively strongly with the extractive distillation composition, and combines with the extractive distillation composition, to produce the bottoms stream, which exits the extractive distillation zone from a lower portion of the distillation zone. The bottoms steam preferably comprises a mixture of the extractive distillation composition and the second hydrocarbon compound. Preferably, the bottoms stream is relatively enriched in the second hydrocarbon compound and relatively depleted in the first hydrocarbon compound, as compared with the feed mixture.

In contrast to the second hydrocarbon compound, the typically less polar first hydrocarbon compound often interacts less strongly with the extractive distillation composition, retains relatively more of it's volatility, and preferentially vaporizes to become relatively enriched in, and form the overhead stream, which typically exits the extractive distillation zone from an upper portion of the extractive distillation zone.

In certain embodiments, wherein the extractive distillation composition comprises a compatibility agent and/or dimethyl sulfone, the bottoms steam acquires an improved capacity for selectively removing the second hydrocarbon compound from the feed material, as gauged by the absolute quantity or mass of the second hydrocarbon compound separated. Viewed in a different way, in the presence of the compatibility agent and/or dimethyl sulfone, the loading of the second hydrocarbon compound in the bottoms stream (as gauged by weight or mole percentage, or other similar measures) increases. Therefore, in embodiments employing the compatibility agents and/or dimethyl sulfone, the bottoms stream may have a higher loading of the second hydrocarbon compound than the loading of the second hydrocarbon compound obtained in the absence of the compatibility agent and/or dimethyl sulfone. High loadings of the second hydrocarbon compound in the bottoms streams are particularly desirable when the second hydrocarbon compound comprises a valuable aromatic compound, or a mixture of aromatic compounds, such as benzene, toluene, xylenes, or mixtures thereof.

In one embodiment, the extractive distillation process further comprises withdrawing the bottoms stream from the lower portion of the extractive distillation zone. In another preferred embodiment, the extractive distillation process further comprises treating the bottoms stream to separate the second hydrocarbon compound from the extractive distillation composition. The treatment which separates the second hydrocarbon compound from the extractive distillation composition often comprises a further distillation or extraction process.

In a preferred embodiment, the feed mixture comprises a mixture of aliphatic and olefinic compounds, wherein the first hydrocarbon compound is an aliphatic compound or mixture of aliphatic compounds, and the second hydrocarbon compound is an olefinic compound or a mixture of olefinic compounds.

In certain embodiments, the first hydrocarbon compound is a $C_7$–$C_{10}$ aliphatic compound. In other embodiments, the saturated hydrocarbon residue of the first hydrocarbon compound comprises at least two carbon atoms.

In addition, the second hydrocarbon compound can comprise an aromatic residue. In more preferred embodiments, the second hydrocarbon compound is a $C_6$–$C_{10}$ substituted benzene compound.

In certain preferred embodiments, the second hydrocarbon compound is benzene, toluene, ortho xylene, meta xylene, para xylene, or a mixture thereof. In one highly preferred embodiment, the feed mixture comprises a BTX stream. BTX streams are very common in petroleum and hydrocarbon refining and recovery processes, and comprise mixtures of benzene, toluene, para-xylene, meta-xylene, ortho-xylene, in mixtures also comprising other saturated hydrocarbons or olefins having normal boiling points similar to those of benzene, toluene, para-xylene, meta-xylene, ortho-xylene. The saturated hydrocarbons of BTX streams typically comprise mixtures of isomeric $C_6$–$C_{10}$ alkanes and/or olefins. In refinery operations, the aromatic compounds generally are of higher value, and the objective of extractive distillation of BTX streams is to selectively purify and/or recover the aromatics from mixtures. A selective extractive distillation solvent often enhances the concentration of aliphatic/non-aromatic materials in the extractive distillate ("raffinate" in refinery parlance) relative to that of the aromatic components.

In another preferred embodiment, the feed mixture comprises ethylbenzene, styrene, or a mixture thereof.

Although extractive distillation is often applied to separate a wide variety of mixtures of hydrocarbon compounds, including very complex multi-component mixtures, and azeotropic mixtures (which form in either the presence or absence of water), extractive distillation is often employed when certain components of the hydrocarbon mixture have similar normal boiling points or volatilities. In preferred embodiments of the processes of the invention, the first and second hydrocarbon compounds have normal boiling points that differ by less than 5° C. More preferably, the first and second hydrocarbon compounds have normal boiling points that differ by less than 2° C.

One preferred embodiment of the invention relates to a process for separating hydrocarbon compounds of similar boiling points by extractive distillation, comprising the steps of:
  a) introducing a feed mixture into an extractive distillation zone having an upper portion and a lower portion, wherein the feed mixture comprises at least
    i) a first hydrocarbon compound comprising a $C_7$–$C_{10}$ aliphatic compound, and
    ii) a second hydrocarbon compound comprising benzene, toluene, ortho xylene, meta xylene, para xylene, or a mixture thereof,
  b) introducing an extractive distillation composition into the upper portion of the extractive distillation zone;
  c) distilling the feed mixture to at least partially separate the feed mixture into an overhead stream rich in the first hydrocarbon compound, and a bottoms stream rich in the second hydrocarbon compound;
  wherein the extractive distillation composition comprises:
    i) about 100 parts by weight of sulfolane or a sulfolane derivative, and
    ii) from about 5 to about 35 parts by weight of a compatibility agent or a mixture of compatibility agents, wherein the compatibility agent comprises an unsubstituted or substituted derivative of acetophenone, propiophenone, benzonitrile, a dialkyl phthalate ester, a cinnamate ester, a $C_6$–$C_{12}$ alkyl ester of acetic, propionic, or butyric acid, a $C_7$–$C_{10}$ methyl alkyl ketone, isophorone, a nitrobenzene, quinoline, or an isoquinoline.

The extractive distillation composition of the above-described process can further comprise dimethylsulfone, in a preferred amount from about 0.1 parts to about 50 parts by weight of dimethylsulfone. The extractive distillation composition of the above-described process can further comprise water, in a preferred amount from about 0.1 parts to about 10 parts of water.

In yet a different aspect, the invention relates to process for separating a mixture of hydrocarbon compounds by extractive distillation that employs an extractive distillation composition, wherein the improvement comprises the use of an extractive distillation composition comprising:
  a) sulfolane and/or a sulfolane derivative, and
  b) at least one compatibility agent, wherein the at least one compatibility agent:
    i) is selected from materials having a Polar Parameter and a Hydrogen Bonding Parameter such that the extractive distillation composition provides improved separation of the hydrocarbon compounds, as compared to the use of sulfolane and/or a sulfolane derivative without the compatibility agent;
    ii) has a boiling point higher than the boiling point of the mixture of hydrocarbon compounds; and
    iii) does not comprise an N-substituted-2-thiopyrrolidone compound or residue.

Additionally, the improvements of the invention have the advantage of ready implementation in existing sulfolane-based aromatic extraction units, which are common in the refineries and manufacturing facilities of the chemical and hydrocarbon industries. The improvements and advantages (such as increased product capacity and lower utility and energy costs) are often obtained at relatively low capital cost. The raw material requirements of the process of this invention also compare favorably with that of conventional sulfolane-based processes.

In alternative aspects, the invention provides the products produced by the extractive distillation processes of the invention. The products of the processes of the invention generally comprise the hydrocarbon compounds separated from the feed mixture. These products include the first hydrocarbon compound, the second hydrocarbon compound, the overhead stream, the bottoms stream, any hydrocarbon compounds produced by further treatment of the overhead or bottoms streams, and the extractive distillation composition recovered after it exits the extractive distillation zone. In many embodiments, any extractive distillation composition so recovered is recycled to an extractive distillation zone. Preferred products of the reaction comprise aromatic compounds, including benzene, toluene, and/or xylenes.

The instant invention provides compositions for the separation of aromatic and aliphatic hydrocarbons that offer improved extraction selectivity, and are more thermally stable than the extractive distillation solvents in use in the hydrocarbon industry. Dimethyl sulfone may be to sulfolane in conjunction with a compatibility agent to sulfolane to achieve these enhancements. Dimethyl sulfone is an extractive distillation solvent of supreme thermal stability. Combinations of dimethyl sulfone and sulfolane offer fluid extraction materials that have longer recycle life due to the enhanced thermal stability of the mixture. Additionally, marked gains in selectivity result from the incorporation of the compatibility agent. Compatibility agents serve to maximize contact between the hydrocarbon mixture and the extraction medium, and thereby optimize extraction efficiency. Use of the compositions containing sulfolane, dimethyl sulfone, and at least one compatibility agent according to the instant invention affords the optimal marriage of extraction selectivity and thermal stability.

Experimental

The following examples are put forth so as to provide those of ordinary skill in the art with a complete disclosure and description of how the compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) But some errors and deviations should be accounted for. Unless indicated otherwise, parts are parts by weight, temperature is in °C. or is at ambient temperature, and pressure is at or near atmospheric.

EXAMPLE 1

The extraction composition were combined in a distillation apparatus designed to condense and collect the extractive distillate. A hydrocarbon mixture containing 0.5 parts by weight of toluene and 0.5 parts of n-heptane were added to the apparatus. Four parts by weight of an extractive distillation composition (of a specified composition comprising sulfolane, compatibility agent, and/or water) was added. The volume of the overall mixture was essentially constant between experiments, to eliminate differences attributable to heating and distillation effects in the apparatus. The mixture was then heated to its boiling point, and a measured volume of the hydrocarbon raffinate was collected, and analyzed using gas chromatography for heptane and toluene. Experiments without compatibility agent (i.e. control experiments) were also performed, and the results compared to experiments which used a compatibility agent.

Selectivity studies. In an experiment typical of the series of experiments summarized in Table 2 and FIG. 2, an extractive distillation composition was prepared by mixing 24.4 g sulfolane, 24.4 g dimethyl sulfone (i.e., 50% sulfolane, 50% dimethylsulfone, see Table 2, row 1, column 1), 1.25 g $H_2O$ and 14.5 g of isophorone compatibility agent were mixed, to give a total of 64.55 grams of the extractive distillation composition, which was added to the experimental distillation apparatus. A feed mixture of 14.5 g of a mixture of 7.25 g toluene and 7.25 g n-heptane was also added to the distillation apparatus. The resulting mixture was carefully distilled and the first 2.0 mL overhead distillate was collected. The resulting distillate analyzed at 85.29% n-heptane (see Table 2, row 1, column 2).

In a comparative experiment, (which did not employ the isophorone compatibility agent) 32.25 g dimethyl sulfone, 32.25 g sulfolane (i.e., 50% sulfolane, 50% dimethylsulfone), and 1.7 g $H_2O$ were mixed to give 66.20 grams of extractive distillation composition. The feed mixture comprised comprised of 8.25 g toluene and 8.25 grams n-heptane. The resulting mixture was again carefully distilled, collecting the first 2.0 mL of the extractive distillate. The resulting distillate analyzed at 77.29% n-heptane (see Table 2, row 1, column 3). Similar experiments were conducted utilizing extractive distillation compositions having lower percentages of dimethyl sulfone, (and correspondingly higher percentages of sulfolane (See Table 2, rows 2–6). The results are plotted in FIG. 2.

TABLE 2

Extractive Distillation of Heptane/Toluene Mixtures with Sulfolane/Dimethyl Sulfone/Water Mixtures, With and Without Isophorone Compatiblizer

| | Sulfolane/DMSO$_2$ | Wt % n-Heptane in Overhead Distillate | |
|---|---|---|---|
| | Ratio % DMSO$_2$ | With Isophorone Compatiblizer | Without Isophorone Compatiblizer |
| 1 | 50.0 | 85.29 | 77.3 |
| 2 | 25.0 | 86.30 | 81.07 |
| 3 | 12.5 | 86.58 | |
| 4 | 6.75 | 87.05 | 81.51 |
| 6 | 2.0 | 86.89 | |

Figure 2:
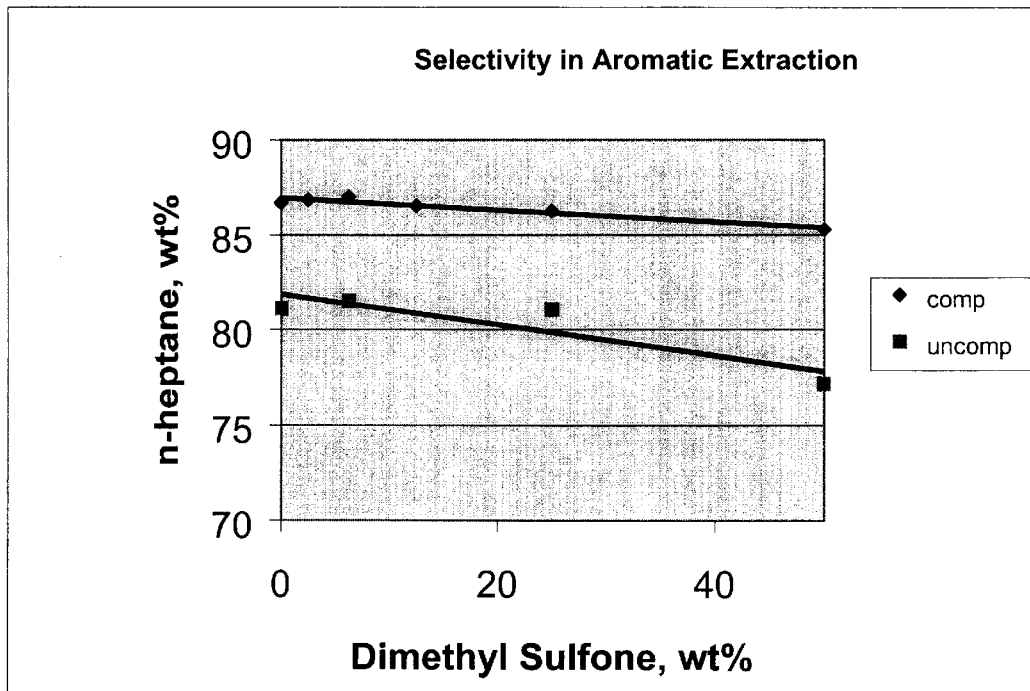
FIG. 2 shows the results of experiments on the selectivity of extractive distillation separation of n-heptane and toluene, in the presence of the extractive distillation compositions of the invention, with and without isophorone compatibility agent, as a function of the weight % of dimethylsulfone versus sulfolane.

As can be seen in FIG. 2, at all weight compositions of sulfolane versus dimethylsulfone, the extractive distillation composition compatibilized with isophorone (denoted in FIG. 2 as "comp") is markedly more selective than the uncompatibilized formulation, (denoted "uncomp"). This phenonenon was observed throughout the range of dimethylsulfone compositions investigated. Thus, an enhancement in selectivity of 6–8% is achieved at all dimethyl sulfone loadings. This improvement is considerable in view of the fact that modest selectivity enhancements may result in substantial economic gains in BTX operations.

EXAMPLE 3

Figure 3:
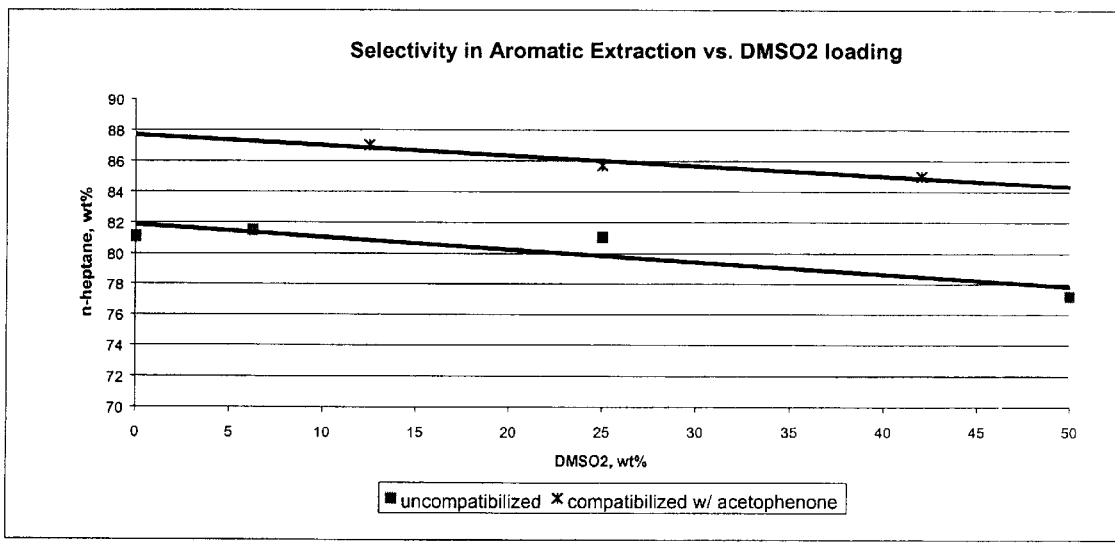
FIG. 3 shows the results of experiments on the selectivity of extractive distillation separation of n-heptane and toluene, in the presence of the extractive distillation compositions of the invention, with and without acetophenone compatibility agent, as a function of the weight % of dimethylsulfone versus sulfolane.

An extractive distillation composition was prepared by mixing 37.5 grams of sulfolane, 12.2 grams of dimethyl sulfone (i.e. 75% sulfolane and 25% dimethyl sulfone), 1.25 grams $H_2O$, and 14.5 grams of acetophenone as a compatibility agent. The extractive distillation composition was charged to an experimental distillation apparatus, along with a feed mixture of 14.5 grams of toluene and 7.25 grams of n-heptane. The resulting mixture was carefully distilled and the first 2.0 mL of overhead distillate was collected. The resulting distillate analyzed at 85.70% n-hepatane. Other similar experiments were conducted using acetophenone as a compatibility agent, and are shown in Table 3 and FIG. 3 below.

TABLE 3

Extractive Distillation of Heptane/Toluene Mixtures with Sulfolane/Dimethyl Sulfone/Water Mixtures, With and Without Acetophenone Compatiblizer

| | Sulfolane/DMSO$_2$ | Wt % n-Heptane in Overhead Distillate | |
|---|---|---|---|
| | Ratio % DMSO$_2$ | With Acetophenone Compatiblizer | Without Acetophenone Compatiblizer |
| 1 | 50.0 | | 77.20 |
| 2 | 42.0 | 84.99 | 77.3 |
| 3 | 25.0 | 85.70 | 81.07 |
| 4 | 12.5 | 87.01 | |
| 5 | 0.0 | | 81.12 |

EXAMPLE 3

Thermal stability studies. The relative thermal stabilities of sulfolane and dimethyl sulfone were compared. Samples of dimethyl sulfone and sulfolane (10.0 g) were placed in 50-ml screw-top vials and placed in an oil bath maintained at 140° C. Commercial samples of dimethyl sulfone and sulfolane were guaranteed at 99% purity. Aliquots of the heated sample were analyzed at 0, 24, 48, and 96 hours by gas chromatography, and the formation of impurities was monitored with time. The results are shown in Table 4, and FIG. 4.

TABLE 4

Thermal Stability of Sulfolane and Dimethyl Sulfone

| | % impurities | |
|---|---|---|
| Time (hr) | Sulfolane | Dimethyl Sulfone |
| 0 | 0.046 | 0.056 |
| 24 | 0.132 | 0.055 |
| 48 | 0.176 | 0.046 |
| 96 | 0.290 | 0.061 |

Figure 4:
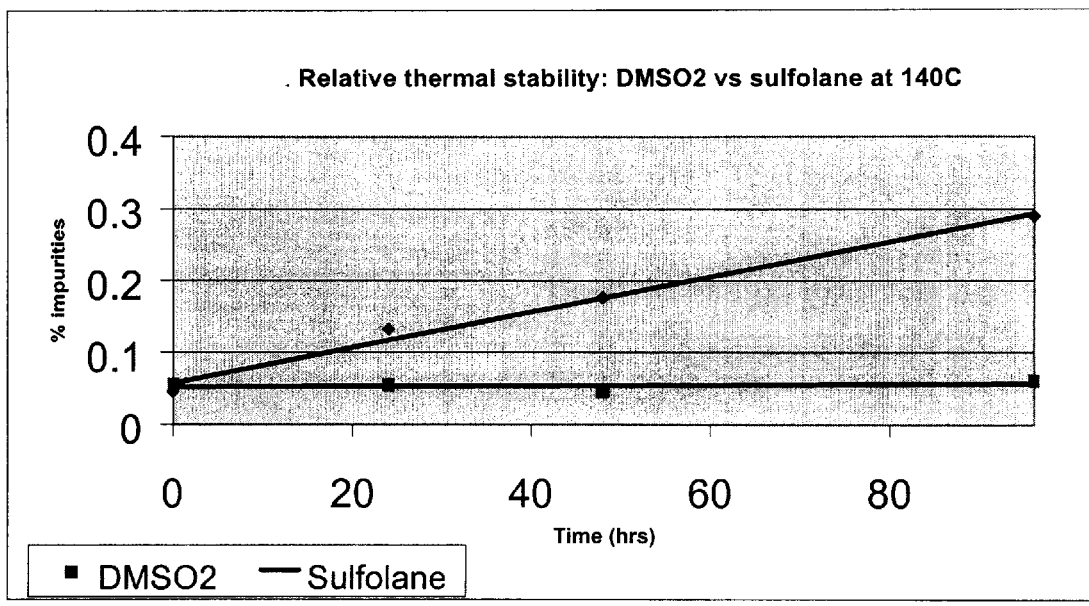
FIG. 4 shows the relative degrees of thermal degradation of sulfolane and dimethylsulfone ("$DMSO_2$") as a function of time.

As evidenced from the data in Table 4 and FIG. 4, dimethyl sulfone is more thermally stable than sulfolane. Over a 96 hr period, only a negligible quantity of impurities were generated in the dimethyl sulfone sample (0.005%). In contrast, the sulfolane sample became quite dark and 25% impurities developed. While this is seemingly a small value, this decomposition becomes problematic (and expensive) when extrapolated to a year's time. Thus, it might be expected that approximately 22.8% of the sulfolane would decompose after 365 days under these conditions. This is a considerable reduction in the recycle life of the sulfolane, which would lead to a need for makeup sulfolane. Therefore, due to its negligible decomposition at this temperature, 50% dimethyl sulfone loading in sulfolane extractive distillation units would be expected to reduce solvent decomposition to about half that currently observed.

Throughout this application, various publications are referenced. The disclosures of these publications in their entirities are hereby incorporated by reference into this application for all purposes.

It will be apparent to those skilled in the art that various modifications and variations can be made without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for separating hydrocarbon compounds of similar boiling points by extractive distillation, comprising the steps of:
   a) contacting a feed mixture with an extractive distillation composition within an extractive distillation zone, wherein the feed mixture comprises at least
      i) a first hydrocarbon compound, and
      ii) a second hydrocarbon compound comprising an aromatic residue; and
   b) distilling the feed mixture to at least partially separate the feed mixture into an overhead stream enriched in the first hydrocarbon compound, and a bottoms stream enriched in the second hydrocarbon compound; and wherein the extractive distillation composition comprises
      i) sulfolane and/or a sulfolane derivative having the formula:

wherein $S_1$, $S_2$, $S_3$, and $S_4$ are independently hydrogen or an alkyl having one to six carbon atoms, and
      ii) at least one compatibility agent, wherein the at least one compatibility agent:
         (1) has a Hansen's Solubility Polar Parameter from about 2.7 to about 6.4 $(calories/cm^3)^{1/2}$, and a Hansen's Solubility Hydrogen Bonding Parameter from about 1.0 to about 4.4 $(calories/cm^3)^{1/2}$;
         (2) has a boiling point higher than the boiling point of the mixture of hydrocarbon compounds; and
         (3) does not comprise an N-substituted-2-thiopyrrolidone compound or residue.

2. The process of claim 1, wherein the at least one compatibility agent has a normal boiling point exceeding about 185° C., a Hansen's Solubility Polar Parameter from about 3.2 to about 5.9 $(calories/cm^3)^{1/2}$, and a Hansen's Solubility Hydrogen Bonding Parameter from about 1.5 to about 3.9 $(calories/cm^3)^{1/2}$.

3. The process of claim 1, wherein the at least one compatibility agent is present in an amount effective to maintain the compatibility agent in a liquid state during extractive distillation.

4. The process of claim 1, wherein the at least one compatibility agent is present in an amount effective to increase the loading of the second hydrocarbon compound in the bottoms stream, as compared with extractive distillation in the absence of the compatibility agent.

5. The process of claim 1, wherein the extractive distillation composition further comprises dimethylsulfone.

6. The process of claim 1, wherein the extractive distillation composition further comprises water.

7. The process of claim 1, wherein the first hydrocarbon compound is a $C_7$–$C_{10}$ aliphatic compound.

8. The process of claim 1, wherein the second hydrocarbon compound is a $C_6$–$C_{10}$ substituted benzene compound.

9. The process of claim 1, wherein the second hydrocarbon compound is benzene, toluene, ortho xylene, meta xylene, para xylene, or a mixture thereof.

10. The process of claim 1, wherein the first and/or second hydrocarbon compounds form an azeotropic mixture.

11. The process of claim 1, wherein the first and second hydrocarbon compounds have normal boiling points that differ by less than 5° C.

12. The process of claim 1, wherein the feed mixture comprises a mixture of aliphatic and olefinic compounds.

13. The process of claim 1, wherein the feed mixture is a BTX stream.

14. The process of claim 1, comprising further treating the bottoms stream to separate the second hydrocarbon compound from the extractive distillation composition.

15. A process for separating hydrocarbon compounds of similar boiling points by extractive distillation, comprising the steps of:
a) introducing a feed mixture into an extractive distillation zone having an upper portion and a lower portion, wherein the feed mixture comprises at least
  i) a first hydrocarbon compound comprising a $C_7$–$C_{10}$ aliphatic compound, and
  ii) a second hydrocarbon compound comprising benzene, toluene, ortho xylene, meta xylene, para xylene, or a mixture thereof;
b) introducing an extractive distillation composition into the upper portion of the extractive distillation zone;
c) distilling the feed mixture to at least partially separate the feed mixture into an overhead stream rich in the first hydrocarbon compound, and a bottoms stream rich in the second hydrocarbon compound;
wherein the extractive distillation composition comprises:
  i) about 100 parts by weight of sulfolane or a sulfolane derivative having the formula:

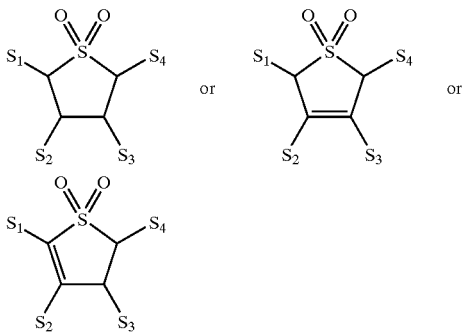

wherein $S_1$, $S_2$, $S_3$, and $S_4$ are independently hydrogen or an alkyl having one to six carbon atoms, and
  ii) from about 5 to about 35 parts by weight of a compatibility agent or a mixture of compatibility agents, wherein the compatibility agent composes an unsubstituted or substituted derivative of acetophenone, propiophenone, benzonitrile, a dialkyl phthalate ester, a cinnamate ester, a $C_6$–$C_{12}$ alkyl ester of acetic, propionic, or butyric acid, isophorone, a nitrobenzene, quinoline, or an isoquinoline.

16. The process of claim 15, wherein the extractive distillation composition further comprises dimethylsulfone.

17. The process of claim 16, wherein the extractive distillation composition further comprises water.

18. A process for separating a BTX stream by extractive distillation that employs an extractive distillation composition, wherein the improvement comprises the use of an extractive distillation composition comprising:
a) sulfolane and/or a sulfolane derivative having the formula:

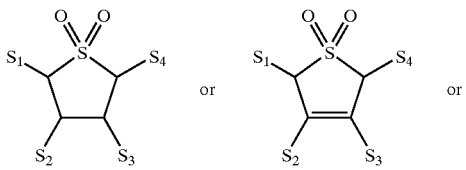

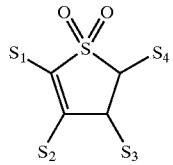

wherein $S_1$, $S_2$, $S_3$, and $S_4$ are independently hydrogen or an alkyl having one to six carbon atoms, and
b) at least one compatibility agent, wherein the at least one compatibility agent:
  i) has a Hansen's Solubility Polar Parameter from about 2.7 to about 6.4 $(calories/cm^3)^{1/2}$, and a Hansen's Solubility Hydrogen Bonding Parameter from about 1.0 to about 4.4 $(calories/cm^3)^{1/2}$:
  ii) has a boiling point higher than the boiling point of the BTX stream; and
  iii) does not comprise an N-substituted-2-thiopyrrolidone compound or residue.

19. The process of claim 18, further comprising dimethylsulfone.

20. The process of claim 18, wherein the at least one compatibility agent has a normal boiling point exceeding about 185° C.

21. The process of claim 18, wherein the at least one compatibility agent has a Hansen's Solubility Polar Parameter from about 3.2 to about 5.9 $(calories/cm^3)^{1/2}$, and a Hansen's Solubility Hydrogen Bonding Parameter from about 1.5 to about 3.9 $(calories/cm^3)^{1/2}$.

22. The process of claim 18, wherein the at least one compatibility agent comprises a substituted or unsubstituted of:
a) acetophenone,
b) propiophenone,
c) benzonitrile,
d) a dialkyl phthalate ester,
e) a cinnamate ester,
f) a $C_6$–$C_{12}$ alkyl ester of acetic, propionic, or butyric acid,
g) isophorone,
h) nitrobenzene,
i) quinoline, or isoquinoline, or
j) a dialkylester of succinic, glutaric, or adipic acids, or mixtures thereof.

23. The process of claim 18, wherein the compatibility agent comprises one or more of acetophenone, benzonitrile, di-n-butyl phthalate, diethyl phthalate, dimethyl phthalate, ethyl cinnamate, a 2-hexyl acetate, isophorone, nitrobenzene, or quinoline.

24. The process of claim 1, wherein the at least one compatibility agent has a normal boiling point exceeding about 185° C.

25. The process of claim 1, wherein the compatibility agent comprises a mixture of two or more materials.

26. The process of claim 1, wherein the at least one compatibility agent has a Hansen's Solubility Polar Parameter from about 3.2 to about 5.9 $(calories/cm^3)^{1/2}$, and a Hansen's Solubility Hydrogen Bonding Parameter from about 1.5 to about 3.9 $(calories/cm^3)^{1/2}$.

27. The process of claim 1, wherein the at least one compatibility agent comprises a substituted or unsubstitute of:

a) acetophenone,
b) propiophenone,
c) benzonitrile,
d) a dialkyl phthalate ester,
e) a cinnamate ester,
f) a $C_6$–$C_{12}$ alkyl ester of acetic, propionic, or butyric acid,
g) isophorone,
h) nitrobenzene,
i) quinoline, or isoquinoline, or
j) a dialkylester of succinic, glutaric, or adipic acids, or mixtures thereof.

28. The process of claim 1, wherein the compatibility agent comprises one or more of acetophenone, benzonitrile, di-n-butyl phthalate, diethyl phthalate, dimethyl phthalate, ethyl cinnamate, a 2-hexyl acetate, isophorone, nitrobenzene, or quinoline.

* * * * *